United States Patent
Reichl et al.

(12)

(10) Patent No.: US 6,201,136 B1
(45) Date of Patent: Mar. 13, 2001

(54) SEPARATION OF LIQUID MIXTURES COMPRISING FORMALDEHYDE, TRIOXANE, ALCOHOL AND HEMIFORMAL

(75) Inventors: Albert Reichl; Michael Kleiber, both of Frankfurt; Michael Rosenberg, Niedernhausen; Dirk Scheid, Waldems; Dieter Sommerfeld, Hünstetten-Beuerbach; Wolfgang Nickelfeld, Frankfurt, all of (DE)

(73) Assignee: Ticona GmbH (DE)

( * ) Notice: Subject to any disclaimer, the term of this patent is extended or adjusted under 35 U.S.C. 154(b) by 0 days.

(21) Appl. No.: 09/436,547

(22) Filed: Nov. 9, 1999

(30) Foreign Application Priority Data

Nov. 9, 1998 (DE) .............................................. 198 51 481

(51) Int. Cl.$^7$ ............................ C07D 323/06; B01D 3/00
(52) U.S. Cl. .............................................. 549/368; 203/74
(58) Field of Search ................................ 549/368; 203/74

(56) References Cited

U.S. PATENT DOCUMENTS 5,766,424 * 6/1998 Arnold et al. ......................... 203/74
6,121,467 * 9/2000 Kniep et al. ......................... 549/368
6,124,480 * 9/2000 Hoffmockel et al. ................ 549/368

FOREIGN PATENT DOCUMENTS

| 133669 | 3/1985 | (EP) . |
| 754689 | 1/1997 | (EP) . |
| WO 9622986 | 8/1996 | (WO) . |

\* cited by examiner

*Primary Examiner*—Deborah C. Lambkin
(74) *Attorney, Agent, or Firm*—Connolly Bove Lodge and Hutz LLP

(57) ABSTRACT

In a process for separating liquid mixtures comprising formaldehyde, trioxane, alcohol, hemiformal formed from the formaldehyde and the alcohol, usual minor components and up to 5% by weight of water, the liquid mixture is distilled batchwise or continuously at reduced pressure, atmospheric pressure or superatmospheric pressure in suitable apparatuses which are to be connected to one another in an appropriate manner, and the trioxane is produced in very high purity. The other materials of value, formaldehyde and alcohol, present in the mixture can likewise optionally be separated off and recycled or used otherwise, while the minor components are ejected.

14 Claims, 1 Drawing Sheet

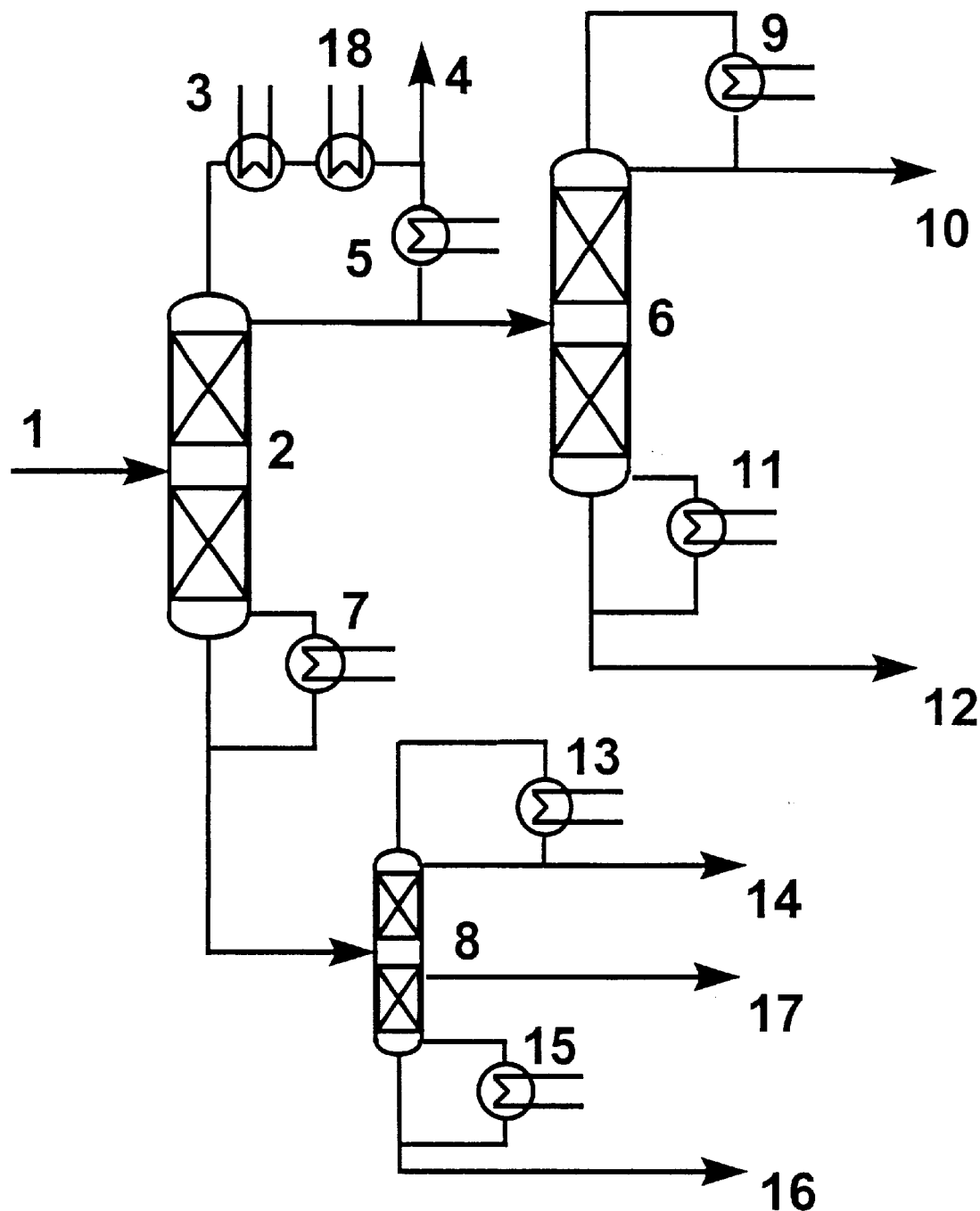
Figure 1 / 1

SEPARATION OF LIQUID MIXTURES COMPRISING FORMALDEHYDE, TRIOXANE, ALCOHOL AND HEMIFORMAL

The invention relates to a process for separating liquid mixtures comprising formaldehyde, trioxane, alcohol, hemiformal formed from the formaldehyde and the alcohol, usual minor components and up to 5% by weight of water. The liquid mixture is distilled batchwise or continuously at reduced pressure, atmospheric pressure or superatmospheric pressure in suitable apparatuses which are to be connected to one another in an appropriate manner, and the trioxane is produced in very high purity. The other materials of value, formaldehyde and alcohol, present in the mixture can likewise optionally be separated off and recycled or used otherwise, while the minor components are ejected.

To prepare engineering plastics, in particular polyacetals such as polyoxymethylene, high-purity trioxane is required. The quality of the plastic, i.e. the achievable degree of polymerization, depends not only on the polymerization conditions but predominantly on the purity of the trioxane.

Various methods are known for preparing trioxane, e.g. using homogeneous or heterogeneous catalysis from aqueous formaldehyde solutions (AT-252913) or heterogeneous catalysis from gaseous formaldehyde in the presence of heteropoly acids (EP-606056). However, regardless of the preparation process, trioxane is never produced as a pure substance but always in a mixture with unreacted formaldehyde, water and small amounts of other components, such as methanol, methyl formate, methylal, formic acid, dioxolane and tetroxane, which are generally termed minor components. For further use of trioxane, for example for polymerization, this must in particular be separated off from the formaldehyde and may contain only small amounts of minor components.

The separation of trioxane from aqueous trioxane/formaldehyde mixtures which contain more than 10% by weight of water is generally current. However, the separation of gaseous mixtures of formaldehyde and trioxane is also known.

Aqueous mixtures have been separated to date in particular via azeotropic distillation (AT-252913 and JP 83-171278). In this process, unreacted formaldehyde can be recirculated to the reactor and there further reacted to form trioxane. However, the azeotrope of trioxane and water which boils at 92° C. and 1 bar and contains approximately 70% by weight of trioxane sets a limiting value on the achievable purity of the trioxane produced by this method. A disadvantage of this method is the danger of solids formation due to polymerization of formaldehyde or formation of paraformaldehyde especially in the region of the column top. To avoid same, all apparatus components must either be heated to temperatures >100° C. (at 1 bar of formaldehyde partial pressure) or be wetted with a liquid.

A further process for separating formaldehyde and trioxane from aqueous solutions is extraction of the trioxane by organic solvents in which trioxane has a higher physical solubility than the formaldehyde. This process is used solely to separate off trioxane from the aqueous phase. As organic extraction media, for example, saturated aliphatic or aromatic hydrocarbons or halogenated hydrocarbons (EP-583907) which are sparingly miscible with water, or not miscible at all, are used. A disadvantage of the extraction is that using the organic solvent an additional auxiliary is introduced into the process and subsequent work-up of the organic phase also is required. A further disadvantage is that considerable proportions of the trioxane also occasionally remain in the aqueous phase. Large amounts of trioxane must therefore be recycled or are lost in the work-up process.

As a further possible method of selective separation from an aqueous phase, crystallization of trioxane from aqueous formaldehyde/trioxane mixtures is described (DE-3508668). The trioxane concentration in the aqueous mixture in this case must be more than 50% by weight.

In the preparation of trioxane by trimerization of formaldehyde from aqueous formalin solutions, generally, the abovementioned processes of azeotropic distillation, extraction and if appropriate crystallization are linked together in a suitable manner in order to obtain trioxane in the high purity required.

For the separation of gaseous formaldehyde/trioxane mixtures, selective absorption processes are known. In these either the formaldehyde is chemisorbed and the trioxane left in the gas phase (GB-1245990) or, vice versa, there is selective physisorption of the trioxane (EP-A-680959). Since no liquid phase has been found in which either only the formaldehyde or only the trioxane is soluble, in the absorption, proportions of the other respective species are also bound. Therefore, in the selective absorption of formaldehyde, a considerable loss of the valuable material trioxane results, whereas in the selective absorption of trioxane, even with this process, the trioxane purity required for the polymerization cannot be achieved.

A process for separating a formaldehyde and trioxane mixture which is present in the gaseous and low-water state is described in the as yet unpublished German Patent Application No. 198 336 20.9. This process comprises absorption in an alcohol and a downstream separation of the trioxane from the alcohol or from the hemiformal by crystallization. The process forms a possible step in a novel process for preparing trioxane from methanol, consisting of the steps of non-oxidative dehydrogenation (DE-3920811), formaldehyde removal (German Patent Applications No. 197 476 47.3 and No. 197 483 80.1), formaldehyde trimerization (EP-A-606056, EP-A-691388) and trioxane removal. However, even the trioxane produced by this process does not have the purity necessary for a polymerization.

The object is to develop a process by which trioxane can be produced in high purity, in particular purity suitable for polymerization. In this process, in particular, the problem of removing trioxane from a liquid trioxane/formaldehyde mixture should be solved. The other materials of value present in the mixture, formaldehyde and alcohol, should likewise as far as possible be able to be separated off and recycled or used in other ways, while the minor components, some of which are harmful for the polymerization, should be ejected.

This object is achieved according to the invention by a liquid mixture of formaldehyde, trioxane, an alcohol, corresponding hemiformals, small amounts of lower- and higher-boiling minor components and a maximum of 5% by weight of water being distilled in a suitable manner in one or more appropriately connected apparatuses at reduced pressure, atmospheric pressure or superatmospheric pressure and thus the trioxane being produced in a highly pure form, it being able to arise, depending on process procedure, as distillate, bottoms product or sidestream takeoff.

The invention therefore relates to a process for producing trioxane, the trioxane being separated off from a liquid mixture comprising trioxane, formaldehyde, alcohol, hemiformals formed from the formaldehyde and the alcohol and a maximum of 5% by weight of water by distillation and produced in highly pure form.

The invention also relates to the use of the highly pure trioxane thus produced for preparing polymers and fuels or for producing formaldehyde by depolymerization of the trioxane.

It is essential for the process according to the invention that the liquid mixture to be separated is low in water or anhydrous, i.e. it generally comprises a maximum of 5% by weight, preferably a maximum of 3% by weight, of water.

The highly pure trioxane produced according to the invention has a purity of at least 95% by weight, preferably at least 97% by weight, and particularly preferably at least 99% by weight of trioxane. Advantageously, the liquid mixture to be separated here has a trioxane content in the range from 70 to 95% by weight, particularly advantageously in the range from 83 to 88% by weight.

The alcohol which is present in the liquid mixture and can in part form hemiformals with the formaldehyde is preferably a monohydric alcohol, e.g. cyclohexanol, methanol, propanol or butanol. However, it is also possible to use other alcohols, including polyhydric alcohols, such as glycerol, diethylene glycol, triethylene glycol, triethanolamine, butanetriol or pentanetriol. It is also possible to use a mixture of different alcohols. However, advantageously, the alcohol should have a higher boiling point than trioxane.

The liquid mixture can also comprise usual minor components which arise in the preparation of trioxane such as methanol, methyl formate, tetroxane, dioxolane, trioxyethers and traces of formic acid. The content of the minor components in the liquid mixture here is generally from 1 to 10% by weight, preferably from 2 to 5% by weight. The minor components can likewise optionally be separated off by a suitable process procedure in separate product streams and produced as liquid or gaseous product streams. This can be achieved in particular by distillation in a plurality of distillation apparatuses connected to one another.

The materials of value present in the liquid mixture, formaldehyde and alcohol, can also be advantageously produced simultaneously in separate product streams by suitable connection of distillation apparatuses and recycled to the process or used otherwise.

The process of the invention can be carried out in a single distillation apparatus or in a plurality of distillation apparatuses connected to one another. These can be operated batchwise or continuously, the continuous mode of operation being preferred. Advantageously, in particular when only one distillation apparatus is used, the distillation apparatuses have a plurality of cooling and condensation zones of differing temperature. By this means, and by the use of a plurality of distillation apparatuses connected to one another, a high purity of the trioxane and the simultaneous production of formaldehyde and alcohol and of the minor components can be achieved. Depending on the process procedure and the connection of the distillation apparatuses, the various product streams arise optionally in the liquid or gaseous state as distillate, bottoms product or sidestream takeoff.

Surprisingly, it has been found that using the process of the invention, in contrast to the known processes for separating off trioxane by distillation, no solids formation occurs in the distillation apparatuses. Apparently, owing to the simultaneous presence of trioxane in the vapor phase, the formation of solid paraformaldehyde in the distillation apparatuses is effectively suppressed.

A particular advantage of the process of the invention is that with appropriate process procedure the formaldehyde present in the in-feed can be produced in the gaseous state and therefore can be recycled, for example, into the formaldehyde trimerization process step mentioned at the outset.

Advantageously, the process of the invention is also suitable for separating off trioxane from a mixture which is present in the liquid and low-water state, as arises in the absorption stage or crystallization stage according to the process described in German Application No. 198 336 20.9 and thus in the abovementioned novel process for preparing trioxane from methanol.

The trioxane prepared by the process of the invention is suitable for all known areas of application such as polymerization to form plastics (e.g. to form polyacetals, in particular polyoxymethylene), preparation of fuels and depolymerization to form formaldehyde, which permits further use for all formaldehyde reactions, in particular if highly pure formaldehyde is required for this.

In contrast to the process according to AT-252913 or JP 83-171278, in the process of the invention, separation by distillation is carried out from a low-water liquid mixture without the use of additional material auxiliaries. I.e. the liquid mixture essentially comprises trioxane, formaldehyde, alcohol, corresponding hemiformals, usual minor components which are formed in the reaction in small amounts and from 0 to 5% by weight of water. In the course of the process, no further substances or auxiliaries are added either. Since the advantage of the novel process overall is the low-water preparation of trioxane, the processes according to AT-252913 and JP 83-171278 are not useful solutions here.

The process of the invention is distinguished from the processes used to date by the following advantages:

very high purity and yield of trioxane,
materials of value formaldehyde, alcohol and hemiformal are obtainable in separate streams taken off from the process and can be recycled or fed to other uses,
ejection of low- and high-boiling impurities,
no material auxiliaries are required,
energetically advantageous owing to energy recovery,
avoidance of solids formation (paraformaldehyde) by simultaneous presence of trioxane in the gas phase and trioxane, alcohol and hemiformal in the liquid phase.

FIG. 1 shows a possible equipment embodiment and apparatus circuit of the process according to the invention: the liquid starting mixture 1 is fed to a distillation apparatus 2 which is here constructed as a column. At the top of the column 2 formaldehyde is taken off as gaseous stream 4 together with some trioxane downstream of the partial condensers 3 and 18. The remaining vapor stream, predominantly comprising trioxane and lower-boilers, is kept in the liquid state by the heat exchanger 5, in part recirculated to the column 2 and in part fed to a second column 6. The liquid remaining in the bottom of the column 2 predominantly comprises alcohol, hemiformal, higher-boiling minor components and trioxane. A part thereof is vaporized in the evaporator 7 and recirculated to the column 2. Another partial stream is fed to a further column 8.

In the column 6 the lower-boiling minor components, for example methanol and water, arise as overhead product after condensation in the condenser 9, but trioxane (which forms an azeotrope with water) also arises in the liquid state. The condensate is in part recirculated to the column 6 and in part taken off as stream 10. The liquid present in the bottom of the column 6 comprises trioxane of very high purity. A part thereof is vaporized in the evaporator 11 and recycled to the column 6. Another partial stream is taken off as stream 12.

In the column 8, the minor components boiling between trioxane and the alcohol predominantly arise in the liquid state as overhead product after condensation in the condenser 13. The condensate is in part recirculated to the column 8 and in part taken off as stream 14. The liquid present in the bottom of the column 8 comprises the higher-boiling minor components. A part thereof is vaporized in the evaporator 15 and recycled to the column 8. Another partial stream is taken off as stream 16. The alcohol is taken off from the column 8 by a liquid or vaporous sidestream takeoff 17.

The column 2 is operated at reduced pressure, atmospheric pressure or superatmospheric pressure (preferably atmospheric pressure). The temperatures in the bottom of the column 2 are between 80 and 200° C., preferably between 110 and 150° C. Under the latter conditions, in the bottom of the column 2, the formaldehyde is in part released from the hemiformals. The temperatures in the partial condenser 3 are between 50 and 140° C., preferably between 70 and 100° C. In the partial condenser 18 temperatures between 40 and 120° C., preferably between 60 and 80° C., are set. The temperatures in the heat exchanger 5 are between 50 and 140° C., preferably between 70 and 100° C.

In the process described, the temperature profile of the partial condensers and heat exchanger at the top of column 2 lead to the fact that the formaldehyde released in the bottom can be taken off at the top in the gaseous state together with some trioxane, the simultaneous presence of trioxane avoiding solids formation (paraformaldehyde) which is frequently a problem in other processes involving formaldehyde. Via a differing temperature profile of the partial condensers and heat exchanger the amount and composition of the gaseous takeoff and the formaldehyde content in the overhead product of column 2 can be controlled.

The column 6 is likewise operated at reduced pressure, atmospheric pressure or superatmospheric pressure (preferably atmospheric pressure). The temperatures in the bottom of column 8 are between 80 and 150° C., preferably between 100 and 130° C. In the top of column 6 temperatures between 0 and 100° C., preferably between 30 and 70° C., occur.

The column 8 is also operated at reduced pressure, atmospheric pressure or superatmospheric pressure (preferably atmospheric pressure). The temperatures in the bottom of column 8 are between 100 and 250° C., preferably between 150 and 180° C. In the top of column 8, temperatures between 80 and 180° C., preferably between 100 and 140° C., occur. The vaporous or liquid sidestream is taken off correspondingly at temperatures between 80 and 250° C., preferably between 130 and 180° C.

The above-described apparatus circuit according to FIG. 1 is only one conceivable variant of the process of the invention. In particular, it is also possible firstly to separate the trioxane from the lower-boilers, and then to separate it from the higher-boilers.

By varying the number and disposition of the sidestream takeoffs, in the process of the invention, likewise differing dispositions of columns are achieved.

A further variant of the process of the invention is the partial recycling of the product streams obtained from one column for the specific alteration of the composition of the feed to this column. Thus, for example, a partial stream may be taken off from the distillate produced at the top of column 2 and admixed to the feed 1. In this manner the content, for example, of trioxane in the feed 1 is altered, which in turn has consequences on the composition of the streams in the column and the product streams from the column 2. Variations in the composition of the feed 1 which are caused by an earlier process step and have adverse consequences on the distillation products may likewise be compensated for in this manner.

In contrast to the continuous process procedure shown in FIG. 1, the work-up by distillation in the process of the invention can also be performed batchwise. An advantage in this case is the repeated use of individual columns for differing separation steps. Disadvantages are the lower throughputs and thus longer production times, assuming equal column sizes.

As a supplementation to the disposition shown in FIG. 1, in the process of the invention an additional work-up of the stream 10 exiting the column 6 can be carried out. In particular methanol, but also trioxane, can be separated off, the latter, for example, by a distillation at altered pressure to overcome the azeotrope with water.

If, in contrast to the disposition shown in FIG. 1, in the process of the invention an alcohol which has a lower boiling point than trioxane is used for the hemiformal formation, other separation steps likewise result. For example, in this case, in a first column trioxane and higher boilers can be separated off from alcohol and lower boilers. In two further columns trioxane and the alcohol are then respectively separated off.

The separation by distillation may be operated in the process of the invention at reduced pressure, atmospheric pressure or superatmospheric pressure. In the reduced-pressure procedure, the distillation proceeds more gently but with reduced throughputs, problems due to leaks and the necessity of vacuum generation. In the superatmospheric procedure, the throughputs are higher and the tendency of formaldehyde to form solids is lower because of the higher temperatures. Disadvantages are the greater formation of minor components, the higher strength of the apparatuses, problems with leaks and the necessity of pressure generation.

The distillation apparatuses used are preferably columns, in particular surface rectifiers, such as packed columns or plate columns, where plate columns have a high hold-up capacity and packed columns have a high specific surface area. Particularly preferred columns are bubble-cap columns, trickle-bed columns, columns having random packings and columns having arranged packings. To achieve as low a column height as possible with high throughputs, preferably columns are used having internals which provide an exchange surface as high as possible, for example having structured packings.

In the process of the invention an advantageous repeated use of the energies may be carried out by internal energy recovery. Thus, for example, in the circuit shown in FIG. 1, in the case of a process procedure with sufficiently differing temperature levels, the waste heat of evaporator 15 may be used for heating evaporator 7 or 11, then for the temperature-control of the partial condensers 3 and 18 and of the heat exchanger 5 and further for the temperature-control of the condenser 9. A further possibility is to utilize the energy removed from condenser 13 to heat the evaporator 11.

The process according to the invention may be illustrated below with reference to some experimental studies. In these the column 2 or the column 6 from FIG. 1 was set up in the laboratory and in each case operated individually continuously at atmospheric pressure. The heating power in the evaporator 7 or 11 was set so that the liquid level in the bottom remained constant and thus the mass balance around the column was met in each case. Samples were taken off from all liquid streams and were analyzed by a gas chromatograph.

Structure of column 2 in the laboratory experiments:
Column sections: of glass DN50, fitted in each of the enrichment and stripping parts with 1 m of structured packing CY from Sulzer
Top: Kaminsky type having three heat exchangers which can be controlled to different temperatures (cf. FIG. 1)
Feed: liquid mixture comprising, inter alia, trioxane, cyclohexanol, formaldehyde, methanol and water. Formaldehyde is predominantly bound therein in the form of cyclohexyl hemiformal. Feed into the column center using a balance/pump/metering controller unit.
Bottom takeoff: using balance/pump/metering controller unit
Product streams at the column top:
a) gaseous
b) liquid (distillate)
Structure of column 6 in the laboratory experiments:
Column sections: of glass DN50, fitted in each of the enrichment and stripping parts with 1 m of structured packing BX from Sulzer
Top: Kaminsky type
Feed: liquid mixture comprising, inter alia, trioxane, formaldehyde, methanol and water. Feed into the column center using balance/pump/metering controller unit
Bottom takeoff: using balance/pump/metering controller unit
Product stream at the column top: liquid (distillate)
In the experimental description hereinafter the following abbreviations are used:
FA Formaldehyde
MeOH Methanol
H2O Water
AS Formic acid
TOX Trioxane
CHOL Cyclohexanol
n.d. not determined
All percentages are percentages by mass.

EXAMPLE 1
Column 2—Experiment HETO4

The evaporator 7 used was a natural-circulation evaporator in which a hold-up of approximately 700 cm$^3$ was established. The partial condensers 3 and 18 were operated at 50° C., but the heat exchanger 5 in contrast at 70° C. The experimental parameters and experimental results are compiled in Table 1.

TABLE 1

Experimental parameters and experimental results in Experiment HETO4

| $T_{Bottom}$ ° C. | $T_{Top}$ ° C. | Reflux ratio g/g | Fraction name | Mass flow rate g/h | FA % | MeOH % | H2O % | TOX % | CHOL % |
|---|---|---|---|---|---|---|---|---|---|
| 117 | 110 | 2:1 | Feed | 750 | 4.5 | 1.2 | 0.3 | 86.7 | 7.3 |
|  |  |  | Bottoms | 102 | 0.2 | <0.1 | 0.05 | 75.7 | 24.0 |
|  |  |  | Distillate | 602 | 2.4 | 1.4 | 0.4 | 95.7 | <0.1 |
|  |  |  | gaseous takeoff |  | approx. 45 | n.d. | n.d. | approx. 55 | n.d. |

The hemiformal is cleaved virtually completely, so that the bottoms product only contains 0.2% of formaldehyde. The distillate is virtually free from cyclohexanol and, in addition to the lower-boilers methanol and water, further comprises 2.4% of formaldehyde.

EXAMPLE 2

Column 2—Experiment HETO5a

The evaporator 7 used was a falling-film evaporator in which a hold-up of approximately 400 cm was established. The partial condenser 3 was operated at 70° C., the partial condenser 18 at 50° C. and the heat exchanger 5 at 70° C. The composition of the gaseous takeoff was measured by online GC. The experimental parameters and experimental results are compiled in Table 2.

TABLE 2

Experimental parameters and experimental results in Experiment HETO5a

| $T_{Bottom}$ ° C. | $T_{Top}$ ° C. | Reflux ratio g/g | Fraction name | Mass flow rate g/h | FA % | MeOH % | H2O % | TOX % | CHOL % |
|---|---|---|---|---|---|---|---|---|---|
| 119 | 109 | 2:1 | Feed | 750 | 6.1 | 1.0 | 0.3 | 87.0 | 5.6 |
|  |  |  | Bottoms | 60 | 0.2 | <0.1 | <0.05 | 76.7 | 23.0 |
|  |  |  | Distillate | 626 | 3.5 | 1.1 | 0.3 | 95.1 | <0.005 |
|  |  |  | gaseous takeoff |  | 64.2 | 0.6 | 0.53 | 34.7 | <0.1 |

Even with the use of an evaporator having a smaller hold-up in comparison with Example 1 and with a somewhat higher hemiformal concentrations in the feed, hemiformal is virtually completely cleaved in the bottoms. Owing to the different temperature control of the heat exchangers at the column top, the formaldehyde concentration in the distillate is higher in comparison with Example 1. The cyclohexanol in the distillate was analyzed using a lower limit of detection of the GC analytical method than in Example 1. It was found that less than 50 ppm of cyclohexanol were present in the distillate. Decreasing the bottoms takeoff rate from approximately 100 g/h in Example 1 to approximately 60 g/h in Example 2 has no effect on the compositions of the product streams.

EXAMPLE 3

Column 2—Experiment HETO5b

The evaporator 7 used was, as in Example 2, a falling-film evaporator in which a hold-up of approximately 400 cm was established. Differing from Example 2, the partial condenser 3 and the heat exchanger 5 were operated at 100° C., while 50° C. was again set at the partial condenser 18. The composition of the gaseous takeoff was measured by online GC. The experimental parameters and experimental results are compiled in Table 3.

TABLE 3

Experimental parameters and experimental results in Experiment HETO5b

| $T_{Bottom}$ ° C. | $T_{Top}$ ° C. | Reflux ratio g/g | Fraction name | Mass flow rate g/h | FA % | MeOH % | H2O % | TOX % | CHOL % |
|---|---|---|---|---|---|---|---|---|---|
| 122 | 109 | 2:1 | Feed | 750 | 6.1 | 1.0 | 0.3 | 87.0 | 5.6 |
|  |  |  | Bottoms | 60 | 0.3 | <0.1 | <0.05 | 62.3 | 37.2 |
|  |  |  | Distillate | 617 | 2.9 | 1.1 | 0.3 | 95.7 | <0.005 |
|  |  |  | gaseous takeoff |  | 57.3 | 0.6 | 0.43 | 41.7 | <0.1 |

Increasing the temperature in the partial condenser 3 and heat exchanger 5 from 70° C. in Example 2 to 100° C. decreases the formaldehyde content in the distillate, which in turn contains less than 50 ppm of cyclohexanol.

EXAMPLE 4

Column 2—Experiment HETO7

The evaporator 7 used was, as in Examples 2 and 3, a falling-film evaporator in which, however, this time a hold-up of approximately 200 cm³ was established. The partial condenser 3 was operated at 95° C., the partial condenser 18 at 60° C. and the heat exchanger 5 at 85° C. The composition of the gaseous takeoff was measured by online GC. The experimental parameters and experimental results are compiled in Table 4.

TABLE 4

Experimental parameters and experimental results in Experiment HETO7

| $T_{Bottom}$ ° C. | $T_{Top}$ ° C. | Reflux ratio g/g | Fraction name | Mass flow rate g/h | FA % | MeOH % | H2O % | AS % | TOX % | CHOL % |
|---|---|---|---|---|---|---|---|---|---|---|
| 125 | 108 | 2:1 | Feed | 750 | 4.8 | 1.1 | 0.3 | 0.073 | 86.9 | 6.9 |
|  |  |  | Bottoms | 100 | 0.3 | <0.1 | <0.05 | 0.106 | 42.3 | 57.4 |
|  |  |  | Distillate | 626 | 2.5 | 1.3 | 0.3 | 0.058 | 95.8 | <0.013 |
|  |  |  | gaseous takeoff |  | 53.7 | 0.85 | 0.46 | <0.1 | 45.0 | <0.1 |

Even with the liquid hold-up in evaporator 7 reduced by about half in comparison with Example 3, the hemiformal in the bottoms is virtually completely cleaved. The minor component formic acid is not formed under the distillation conditions. Less than 130 ppm of cyclohexanol are present in the distillate.

EXAMPLE 5

Column 6—Experiment 980819-DST

The feed to the column in this experiment corresponded approximately to the stream produced at the top in column 2 (cf. FIG. 1), termed distillate in Examples 1 to 4. The evaporator 11 used was a natural-circulation evaporator in which a hold-up of approximately 700 cm was established. The temperature of the column top was controlled to 62° C. The experimental parameters and experimental results are compiled in Table 5.

TABLE 5

Experimental parameters and experimental results in Experiment 980819-DST

| $T_{Bottom}$ ° C. | $T_{Top}$ ° C. | Reflux ratio g/g | Fraction name | Mass flow rate g/h | FA % | MeOH % | H2O % | TOX % |
|---|---|---|---|---|---|---|---|---|
| 114 | 97 | 30:1 | Feed | 600 | 2.2 | 1.7 | 0.5 | 95.6 |
|  |  |  | Bottoms | 566 | 0.06 | <0.01 | 0.07 | 99.9 |
|  |  |  | Distillate |  | 9.6 | 11.7 | 3.3 | 75.5 |

The bottoms product obtained is high-purity trioxane. At the same time the lower boilers are separated off with the distillate.

Owing to the surprisingly good cleavage of the cyclohexyl hemiformal in the bottom of column 2, a gaseous takeoff may be produced there which can be recycled, for example, into the process step formaldehyde trimerization. In addition, the virtually formaldehyde-free bottoms product can likewise be reused. This is a particular advantage of the process according to the invention.

Instead of the columns used in Examples 1 to 5 which were fitted with structured packings, in all of the distillation apparatuses available in the process according to the invention the use of other internals (e.g. plates or random packings) is also conceivable, but preferably those which have a high specific surface area.

The stream taken off at the bottom of column 2 which comprises cyclohexanol, trioxane and higher boilers is fractionated in column 8. The design of column 8 is very critically dependent on the by-products spectrum in the bottoms stream.

LIST OF DESIGNATIONS

1 Starting mixture feedline
2 Column
3 Partial condenser
4 Takeoff for the gaseous mixture comprising formaldehyde and trioxane
5 Heat exchanger
6 Column
7 Evaporator
8 Column
9 Condenser
10 Lower-boiling minor-component takeoff
11 Evaporator
12 High-purity trioxane takeoff
13 Condenser
14 Takeoff for the minor-components boiling between trioxane and alcohol
15 Evaporator
16 Higher-boiling minor-component takeoff
17 Alcohol takeoff
18 Partial condenser

What is claimed is:

1. A process for producing trioxane comprising separating off the trioxane from a liquid mixture containing trioxane, formaldehyde, alcohol, hemiformals formed from the formaldehyde and the alcohol and a maximum of 5% by weight of water by distillation and thereby producing a highly pure trioxane.

2. The process as claimed in claim 1, wherein the liquid mixture has a trioxane content in the range of from 70 to 95% by weight and the highly pure trioxane produced has a trioxane content of at least 95% by weight.

3. The process as claimed in claim 2, wherein the liquid mixture has a trioxane content in the range of from 83 to 88% by weight.

4. The process as claimed in claim 2, wherein the highly pure trioxane produced has a trioxane content of at least 99% by weight.

5. The process as claimed in claim 1, wherein the formaldehyde and the alcohol are separated off simultaneously in separate product streams.

6. The process as claimed in claim 1, wherein the liquid mixture comprises usual minor components which arise in the preparation of trioxane and are separated off in separate product streams.

7. The process as claimed in claim 1, wherein the highly pure trioxane and optionally other product streams are optionally produced in the liquid or gaseous state.

8. The process as claimed in claim 1, wherein the distillation is optionally carried out continuously or batchwise at reduced pressure, atmospheric pressure or superatmospheric pressure in a single distillation apparatus or in a plurality of distillation apparatuses connected to one another.

9. The process as claimed in claim 8, wherein the distillation apparatuses have a plurality of cooling and condensation zones of differing temperature.

10. The process as claimed in claim 1, wherein the liquid mixture (1) is fractionated in a first distillation apparatus (2) into two fractions, of which one comprises the trioxane and the lower-boiling components and the other comprises the higher-boiling components, and the fraction comprising the trioxane and the lower-boiling components is again fractionated in a second distillation apparatus (6) into two fractions, of which one (12) comprises trioxane at high purity and the other (10) comprises the lower-boiling components.

11. The process as claimed in claim 10, wherein, in the first distillation apparatus (2), a further fraction arises which is gaseous and essentially comprises formaldehyde.

12. The process as claimed in claim 10, wherein the fraction comprising the higher-boiling components which is produced in the first distillation apparatus (2) is fractionated in a further distillation apparatus (8) into two or more fractions, one fraction comprising the alcohol or the hemiformal in utilizable form, and the other fractions comprising the minor components.

13. A method of use of the trioxane produced by a process as claimed in claim 1 having a trioxane content of at least 95% by weight for preparing polymers and fuels or for producing formaldehyde by depolymerization.

14. The process as claimed in claim 1 further comprising producing a polymer, fuels or highly pure formaldehyde from the highly pure trioxane.

* * * * *

UNITED STATES PATENT AND TRADEMARK OFFICE
CERTIFICATE OF CORRECTION

PATENT NO. : 6,201,136 B1  
DATED : March 13, 2001  
INVENTOR(S) : Albert Reichl, Michael Kleiber, Michael Rosenberg, Dirk Scheid, Dietr Sommerfeld, and Wolfgang Nickelfeld It is certified that error appears in the above-identified patent and that said Letters Patent is hereby corrected as shown below:

Column 8,  
Line 40, "cm" should read -- $cm^3$ --.

Column 9,  
Line 14, "cm" should read -- $cm^3$ --.

Column 10  
Line 17, "cm" should read -- $cm^3$ --.

Signed and Sealed this

Second Day of October, 2001

Attest:

NICHOLAS P. GODICI  
Attesting Officer    Acting Director of the United States Patent and Trademark Office